United States Patent [19]

Burr

[11] 4,282,745
[45] Aug. 11, 1981

[54] PARTICLE SIZE DETERMINATION

[75] Inventor: Kenneth J. Burr, St. Austell, England

[73] Assignee: English Clays Lovering Pochin & Company Ltd., St. Austell, England

[21] Appl. No.: 22,944

[22] Filed: Mar. 22, 1979

[30] Foreign Application Priority Data

Mar. 28, 1978 [GB] United Kingdom ............... 12119/78

[51] Int. Cl.³ ...................... G01N 15/04; G01N 23/12
[52] U.S. Cl. ................................ 73/61.4; 73/432 PS; 250/393
[58] Field of Search .......................... 73/432 PS, 61.4; 356/440, 441, 335; 250/393, 222 PC

[56] References Cited

U.S. PATENT DOCUMENTS

| Re. 27,866 | 1/1974 | Adler ............................... 356/441 X |
| 3,519,353 | 7/1970 | Franz et al. ................. 73/432 PS X |
| 3,621,243 | 11/1971 | Olivier ............................. 250/293 X |
| 3,695,763 | 10/1972 | Shiuh ............................. 356/441 X |
| 3,811,780 | 5/1974 | Liston ................................... 356/244 |
| 3,829,221 | 8/1974 | de Mendez et al. .................. 356/440 |
| 4,041,502 | 8/1977 | Williams et al. .................. 73/61.4 X |

OTHER PUBLICATIONS

Publ. "A New X-Ray Sedimentometer", by Allen et al., Journal of Physics on Scientific Instruments, (1970), vol. 3, pp. 458-460.

Primary Examiner—Daniel M. Yasich
Attorney, Agent, or Firm—Weingram & Klauber

[57] ABSTRACT

In order to determine the proportion of particles of less than a predetermined size in a fluid suspension, the fluid suspension is placed in a vessel (1) and is thoroughly mixed therein by mixing means (36,37). A sample of suspension is then withdrawn from a predetermined level within the vessel (1) by means of a sampling tube (9) and is transferred by way of a flexible tube (22) to a container (15). The particle concentration of this sample is then monitored by passing x-rays from a source (17) through the container (15) and detecting the emerging x-rays with a detector (18). The sample is then drained from the container (15). After allowing the suspension in the vessel (1) to settle for a time sufficient to enable particles of said predetermined size to sink from the surface of the suspension to said predetermined level within the vessel (1) according to Stokes' law, a further sample of suspension is withdrawn from said predetermined level and transferred to the container (15). The x-ray monitoring process is then repeated with this further sample. The complete testing cycle takes place automatically under the control of a control system coupled to a plurality of motors (such as 6) and valves (25, 28, 30, 34).

18 Claims, 3 Drawing Figures

PARTICLE SIZE DETERMINATION

BACKGROUND OF THE INVENTION

This invention relates to apparatus for determining the proportion of particles of less than a predetermined size in a fluid suspension.

In many industries it is required to measure the particle size parameters of particulate solid materials and, in the research and quality control laboratories of such industries, it is often necessary to obtain information quickly and accurately about the particle size distribution of a large number of samples. Information concerning the proportion of particles having a linear dimension greater than about 50 microns is generally most conveniently obtained by the use of test sieves of different aperture sizes. However, when it is required to know the percentage by weight of particles smaller than about 50 microns, it is generally necessary to use a method based on gravitational or centrifugal sedimentation. By Stokes' Law, the particles suspended in a fluid, assuming that they are deflocculated, i.e., are present as discrete particles and not as agglomerates containing particles of different sizes, in the absence of turbulence each fall through the suspension at a velocity which reaches a constant value dependent on the square of the particle radius (assuming that the particle is spherical), the difference between the density of the particle and the density of the fluid and the viscosity of the fluid. When particles are not spherical a true determination of exact particle size is not possible by this method, but the results which are obtained in terms of "equivalent spherical diameter" are nevertheless very useful in comparing the particle size distributions of material having similar particle shape.

It is known to determine the proportion of particles in a suspension of less than a predetermined size by thoroughly mixing the suspension, withdrawing a sample from a particular level within the suspension by means of a pipette, evaporating the sample to dryness, and weighing the resultant dry solid material; and then allowing the suspension to settle under quiescent conditions for the time which according to Stokes' Law is required for particles of the predetermined size to fall from the surface of the suspension to the particular level, withdrawing a second sample from that level, and evaporating and weighing that second sample, the weight obtained in the second step being expressed as a percentage of the weight obtained in the first step to give the required proportion. However such a procedure is time consuming and requires considerable skill if accurate and repeatable results are to be obtained.

SUMMARY OF THE INVENTION

According to the present invention, there is provided apparatus for determining the proportion of particles having a size of less than a predetermined size in a fluid suspension, which apparatus comprises:

(a) at least one vessel for containing the fluid suspension;

(b) mixing means for thoroughly mixing the suspension in the vessel;

(c) a container connected to sampling means;

(d) transfer means for enabling said sampling means to selectively withdraw samples of the suspension from a predetermined level within the vessel and for transferring the samples to the container before and after settling for a pre-selected time in said vessel respectively, the relationship between said predetermined level and pre-selected time being such as to permit particles of said predetermined size to sink from the surface of the suspension to said predetermined level according to Stokes' law;

(e) means for monitoring the particle concentration within the container; and (f) control means for controlling the transfer means (i) so that the sampling means withdraws from said vessel a first sample of thoroughly mixed suspension from said predetermined level and the first sample is transferred to the container for monitoring and for draining and flushing the first sample after monitoring, and (ii) so that the sampling means withdraws from said vessel a second sample of suspension taken from the same pre-determined level as was the first sample for monitoring after allowing the suspension in said vessel to settle for said pre-selected time sufficient to enable particles of said predetermined size to sink from the surface of the suspension to said predetermined level within the vessel according to Stokes' law.

The apparatus advantageously includes a plurality of vessels for containing fluid suspension and the control means is adapted to control the transfer means (i) so that sampling means withdraws a first sample of suspension from each vessel in turn and each first sample is transferred to the container for monitoring and (ii) so that the sampling means withdraws a second sample of suspension from each vessel in turn after said time and each second sample is transferred to the container for monitoring.

Preferably the sampling means comprises a sampling tube and motor means for placing each vessel in turn below the sampling tube. Conveniently the vessels are arranged about a circle and the motor means is adapted to rotate the arrangement of vessels to bring each vessel in turn below the sampling tube. Furthermore the sampling means prefereably further includes lowering means for lowering the inlet of the sampling tube to said predetermined level within each vessel.

Advantageously the sampling tube is closed at its lower end and the inlet is in the form of a plurality of holes in the curved wall of the tube in the vicinity of the lower end, the holes being distributed about the circumference of the tube such that all the holes lie at said predetermined level during sampling.

The monitoring means may comprise an x-ray source for passing x-rays through a sample in the container and an x-ray detector for detecting the x-rays which emerge from the container, under control of the control means, at least parts of the container being transparent to x-rays.

The x-ray source may be a small quantity of radioactive material in a suitable container or an x-ray tube. The x-ray detector may comprise a scintillation counter, a proportional counter or a geiger counter. Conventional electronic circuitry may be used to display the x-ray count. It is not essential to use x-ray absorption to monitor the particle concentration. It is also possible to monitor the specific gravity, and hence the particle concentration, of a small sample of suspension by, for example, measuring the frequency of oscillation of a U-shaped tube containing the sample which frequency depends upon the weight of the sample. The specific gravity is not linearly related to the percentage by weight of solids so, as in the case of x-ray absorption determination, some arithmetical manipulation of the measurements is required in order to calculate the percentages.

The transfer means conveniently includes a pump coupled to the container for providing suction to draw samples into the container. The pump may also be adapted to apply positive pressure to the interior of the container so as to discharge samples from the container by way of a valve.

The control means is preferably adapted not only to cause samples of suspension to be transferred to the container but also to control movement of the sampling tube and rotation of a water bath for the vessel(s), as well as discharge of suspension from the container and rinsing of the container. Furthermore the control means may be adapted to process the data collected and to display the results, preferably in the form of the percentage by weight of particles in each suspension having sizes less than the predetermined size. Conveniently the control means includes a digital data processing unit and means for printing out the results.

BRIEF DESCRIPTION OF THE DRAWINGS

In order that the present invention may be more fully understood, reference will now be made, by way of example, to the accompanying drawings, in which.

DETAILED DESCRIPTION OF THE DRAWINGS

Figure 1:
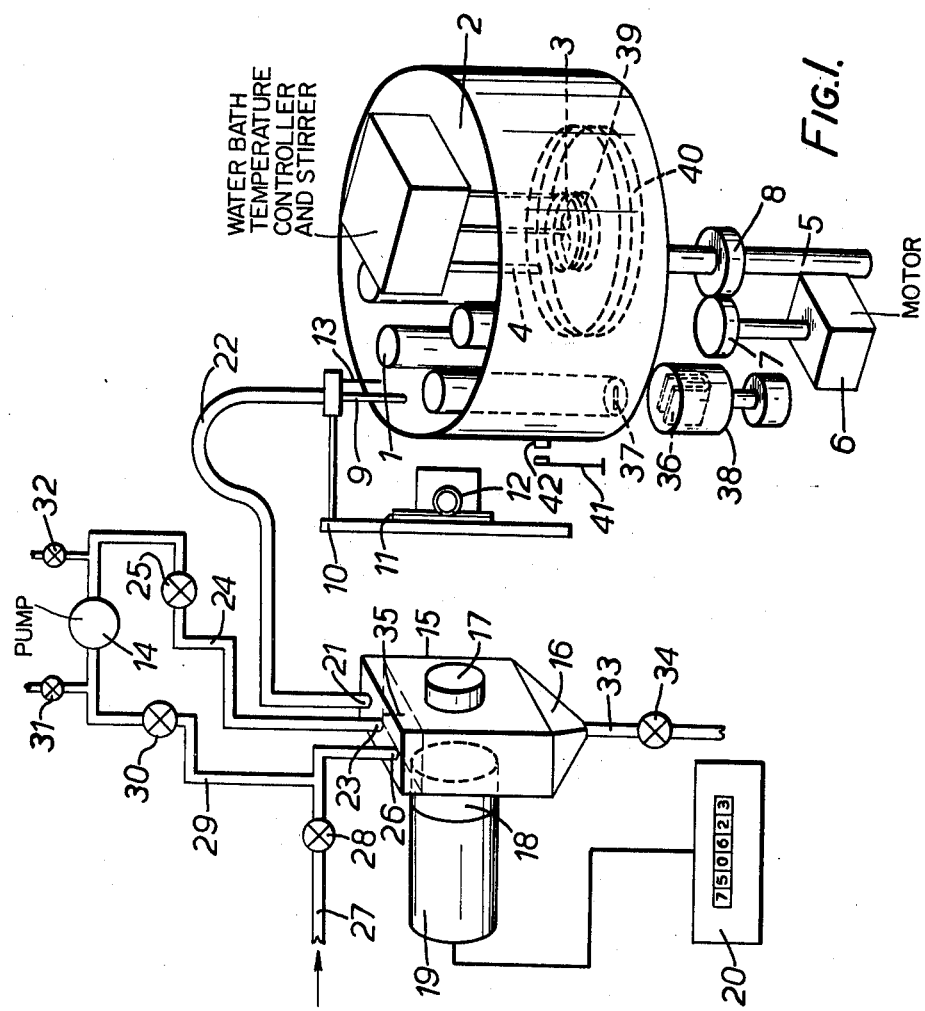
FIG. 1 is a diagrammatic sketch of an embodiment of apparatus in accordance with the present invention.

The particular embodiment shown in the drawings is designed to measure the percentage by weight of particles having equivalent spherical diameters less than one or more predetermined values in the range 0.5–5.0 microns, in a number of suspensions. For example, the embodiment could be used to measure the percentage by weight of particles having equivalent spherical diameters less than 2 microns in a number of kaolinitic clay suspensions. However, similar apparatus can be used in connection with a wide range of different materials and different particle sizes. The apparatus illustrated may be used to determine, in a single testing operation cycle, the percentages of particles in a suspension having sizes less than up to three different values. The apparatus is designed to measure the x-ray absorption of a quantity of each suspension taken from a predetermined level within the suspension, after mixing, and then to measure the x-ray absorption of a further quantity of each suspension taken from the same predetermined level within the suspension after the suspension has been allowed to sediment for a predetermined period of time, one or two further measurements of further quantities optionally being carried out after further sedimentation has taken place.

To load the apparatus, dilute aqueous suspensions of, for example, the kaolinitic clays to be tested are prepared and poured into glass cylindrical vessels 1. The initial solids content of the suspensions is in the range from 2 to 10% by weight, and preferably in the range from 4 to 8% by weight. If the solids content were below 2% by weight, the accuracy of the determination would be unacceptable for most purposes, whereas, if the solids content were above 10% by weight, settling of the particles begins to be hindered. Each suspension is fully deflocculated by adding the appropriate quantity of dispersing agent and the contents of each vessel 1 are then placed in a cylindrical water bath 2 provided with temperature control means comprising water circulating means in the form of a stirrer 3, a thermostat 4 and a heating coil 39 to maintain the temperature of the water accommodated in the water bath 2, each vessel 1 being located in a circular depression in the base of the bath 2.

The number of vessels 1 containing suspensions to be tested is written into a memory location in a digital data processing unit (not shown). This is effected as follow. A reference number of up to 4 decimal digits is entered into the processing unit for each suspension to be tested by means of a digital keyboard and confirmed before entry on a digital display. The reference number is written into the processing unit in binary coded decimal (BCD) form, and, as each reference number is entered, a count of the number of vessels containing suspensions to be tested stored in said memory location is increased by one. The number of size determinations (up to three with the present embodiment) to be performed on each suspension and the appropriate sedimentation times (the purpose of which will be explained hereinafter) in minutes are also entered at this stage by means of the same digital keyboard and digital display. The numbers are written into the processing unit in binary coded decimal form and the sedimentation times are converted by the processing unit to binary seconds.

The water bath 2 is rotatable on a vertical spindle 5 which is driven by motor means in the form of a stepping motor 6 capable of turning the spindle 5 through gear wheels 7 and 8 in a series of small, discrete, angular steps in response to a pulsed signal from a power supply (not shown). The position of the water bath 2 is accurately determined by the number of pulses which are fed to the stepping motor 6.

Figure 2:
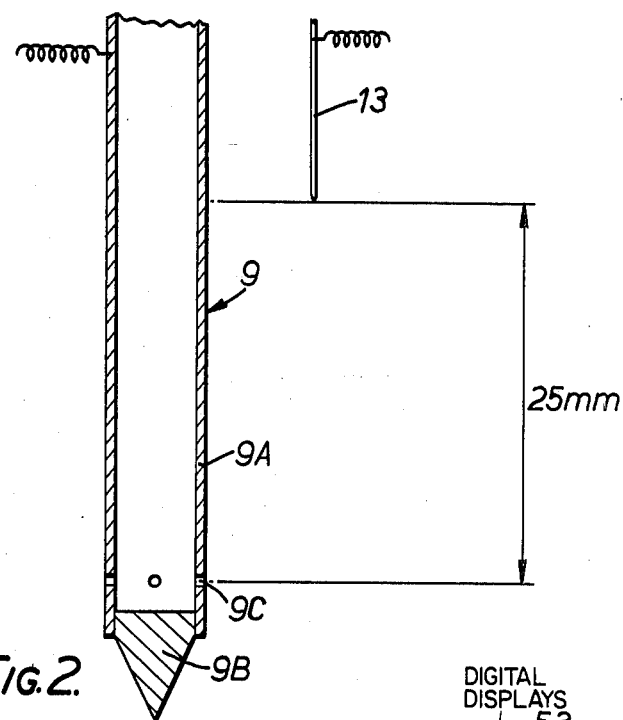
FIG. 2 is a section through a detail of FIG. 1, on an enlarged scale.

A sampling tube 9 mounted on lowering means in the form of a bracket 10 capable of being moved upwards and downwards by a rack 11 and pinion 12 is positioned so that it can be lowered into the open top of one of the vessels 1 located immediately below the sampling tube 9 in the water bath 2. As shown in FIG. 2, the sampling tube 9 comprises a metal tube 9A with a pointed metal plug 9B at the lower end. The tube 9A and plug 9B may be made of stainless steel. A fraction of the sample in the vessel into which the tube is lowered may be drawn into the tube through an inlet in the form of a plurality of holes 9C distributed around the tube in a common horizontal plane. It has been found that this arrangement enables the sample which is drawn into the tube to more nearly correspond to a thin horizontal section through the suspension in the vessel than would be the case if the sampling tube were provided with a single inlet at its tip. A level probe 13 also forming part of the lowering means is provided to sense when the holes 9C in the sampling tube 9 are at the desired depth below the surface of the suspension i.e., at a predetermined level. When the tip of the probe 13 contacts the surface of the suspension in the vessel, it makes electrical contact through the electrically conductive water with the sampling tube 9, thus serving to open a switch which halts the downward motion of the sampling tube. The holes 9C have a diameter of the order of 1 mm (0.5–2.0 mm).

A diaphragm pump 14 is provided for applying positive air pressure or suction to the interior of a test container 15 according to which side of the pump is connected to the container. The container 15 is of rectangular cross-section, has a funnel-shaped bottom portion 16 and is constructed of brass with the two large rectangular faces made of sheet material which is transparent to x-rays, for example diethylene glycol bis(allylcarbonate) sheet material. The parts of the container which are transparent to x-rays may also be transparent to light. The dimensions of the container 15 are approximately 25 mm×15 mm×40 mm. An x-ray beam may be passed through the container 15 from one large face to another from a plutonium 238 source 17 to a detector crystal 18. A photomultiplier 19 is provided to convert the scintillations from the crystal into electrical impulses and an electronic scaler/timer 20 gives a digital display of the x-ray count obtained over a given period divided, if necessary, by a suitable factor.

The top of the container 15 is provided with three ports. Port 21 is connected by a flexible tube 22 to the sampling tube 9, port 23 is connected by a conduit 24 incorporating a valve 25 to the suction side of the pump 14 and port 26 is connected (i) by a conduit 27 incorporating a valve 28 to a low pressure water supply via a coil 40 which is immersed in the water bath 2 to bring the temperature of the water supply close to that of the bath 2, and (ii) by the conduit 27 and a conduit 29 incorporating a valve 30 to the positive pressure side of the pump 14. The port 26 communicates with a plurality of apertures discharging towards the transparent sides of the container 15. A bleed valve 31 allows a little air to be discharged by the pump 14 when the valve 30 is closed and a bleed valve 32 allows a little air to enter the suction side of the pump when the valve 25 is closed, so that at no time is either the suction or the delivery of the pump completely closed. The bottom of the container is provided with a conduit 33 incorporating a drain valve 34. The valves 25, 28, 30 and 34 are automatically actuatable by solenoids.

In operation the fully deflocculated aqueous suspensions contained in the vessels 1 are allowed to remain in the water bath 2 for 1 hour before any measurement is made in order that the suspensions may reach the temperature of the bath, usually 25° C. Alternatively, the suspensions contained in the vessels 1 may be placed in a separate static water bath at the same temperture for at least one hour, so that the water bath 2 is occupied only for the time required for sampling and sedimentation, and is therefore available for a second batch of suspensions. An automatic cycle of testing operations is then started and the valve 28 is opened to allow water to flow into the container 15. The water level rises until it reaches detecting means in the form of a probe 35 at which point the valve 28 is closed. X-rays are then passed through the water in the container 15 from the source 17 so that the emerging x-rays are incident on the detector crystal 18. The number of scintillations induced over a predetermined interval, which may be varied but is usually about 60 seconds, is counted by means of the photomultiplier 19 and displayed in digital form, reduced by a factor of ten, by the scaler/timer 20. The number displayed is also written into locations in the memory of the data processing unit.

The drain valve 34 and valve 30 are opened to discharge the water from the container 15 and the conduit 27. Valves 30 and 34 are then closed and the sampling tube 9 is lowered into the suspension contained in a vessel 1 immediately below it until the probe 13 contacts the surface of the suspension. The contents of the vessel in this position are kept thoroughly mixed by mixing means in the form of a rotating horseshoe magnet 36 disposed beneath the vessel 1 co-operating with one of a number of magnet followers in the form of small bars 37 of ferromagnetic material, a respective one of which is disposed in the bottom of each vessel 1. A steel screen 38 extends around the rotating magnet 36 so that the ferromagnetic bars 37 in the vessels 1 on either side of the vessel 1 immediately above the magnet 36 are not affected by this magnet 36. The valve 25 is then opened to draw suspension under suction through the sampling tube 9 and flexible tube 22 into the container 15 until the level of suspension in the container 15 reaches the probe 35, when valve 25 is closed. About 16 ml of suspension is drawn into the container 15 where the container has the dimensions given above.

The volume of suspension drawn into the container 15 must be large enough to give an accurately measurable x-ray count in a reasonable time but not so large that a substantial depth of sample in the vessel 1 is drawn off. The reason for this may be explained as follows. In a given time, according to Stokes' Law, all particles in a suspension larger than a given equivalent spherical diameter will have fallen below a given horizontal plane. In addition all particles larger than a slightly greater equivalent spherical diameter will have fallen below a lower horizontal plane a short distance below said given plane, and all particles larger than a slightly smaller equivalent spherical diameter will have fallen below an upper horizontal plane a short distance above said given plane. If all the suspension between the upper and lower planes was drawn into the container 15, a measurement of the density of the suspension in the container 15 would therefore give a measure of the number of particles in the original suspension smaller than a size varying over a range, the extent of which depends on the distance between the upper and lower planes. For example, if the diameter of the vessel is 50 mm and the depth at which the sample is taken is 25 mm, the volume of suspension drawn into the container 15, i.e. 16 ml, would represent a depth of suspension in the vessel 1 of 8 mm and a range of particle sizes of from 0.92 to 1.08 times the nominal particle size.

X-rays are then passed through the suspension in the container 15 from the source 17 so that emerging x-rays are incident on the detector crystal 18. The number of scintillations induced over the predetermined interval is counted by means of the photomultiplier 19 and the resulting number displayed digitally by the scaler 20 and also written into the memory of the data processing unit. Meanwhile the rotating magnet 36 is switched off, the sampling tube 9 is raised and the valve 30 is opened to blow surplus suspension in the flexible tube 22 and sampling tube 9 back into the vessel 1. At the completion of the x-ray count, valve 34 is opened to drain the container 15, valve 30 is closed and the walls of the container 15 are rinsed by opening valve 28.

The water bath 2 is then advanced through an angle of 18° by supplying to the stepping motor 6 the required number of pulses. This brings the next vessel 1 beneath the sampling tube 9. The contents of this vessel 1 are thoroughly mixed by the rotating magnet 36 and the steps of drawing a sample of the suspension into the container 15, determining the x-ray count and flushing out the container 15 and associated conduits are repeated with this vessel 1. This procedure is followed with each vessel 1 in turn until the number of vessels 1 indicated in the processing unit has been dealt with. A second x-ray count with the container 15 full of water is then performed and the result written into the memory.

If the water bath 2 is not then back in its starting position, i.e. if the number of vessels 1 is less than twenty, the stepper motor 6 continues to rotate until the first vessel 1 is again under the sampling tube 9. The rotation is stopped by a reed switch 41 actuated by a magnet 42 on the outer wall of the water bath 2 near the first vessel 1.

The contents of the vessels 1 are then allowed to sediment for the required time. In the case of a determination of the proportion by weight of particles having equivalent spherical diameters less than 2 microns in an aqueous suspension of kaolinitic clay at 25° C., this time is about 95 minutes for a depth of the holes 9C in the sampling tube 9 below the surface of the suspension of 22 mm during sampling. However the time could be about 3 hours 26 minutes for a depth of 50 mm; although the higher depth for sampling is advantageous since it decreases the time required for obtaining the desired particle size information without seriously prejudicing the accuracy of the determination. The contents of each vessel 1 are then sampled again and the x-ray count determined as described above except that the rotating magnet 36 is not used. An x-ray count with water in the container 15 is also taken at the beginning and at the end of the sequence of x-ray counts on these suspension samples.

If desired more than one size determination may be performed on each suspension by allowing the contents of each vessel 1 to sediment for an additional time after the second sample of suspension has been withdrawn from each vessel 1, the additional time being sufficient to enable particles greater than a second (smaller) predetermined size to sink below the predetermined level according to Stokes' Law, and sampling the contents of each vessel 1. If desired a third sedimentation step and a fourth sampling step may also be performed.

The x-ray counts which are stored in memory locations in the data processing unit in BCD form may be represented by the symbols:

$$W_1, C_1, C_2, C_3 \ldots C_N, W_2, W_1', C_1', C_2', C_3' \ldots C_C', W_2'$$

where $W_1$, $W_2$ represent the initial and final counts on water taken prior to sedimentation;

$C_1$, $C_2$, $C_3$ - - - $C_N$ represent the counts taken on the samples drawn from each of the N vessels, prior to sedimentation;

$W_1'$, $W_2'$ represent the initial and final counts on water taken after sedimentation; and $C_1'$, $C_2'$, $C_3'$ . . . $C_N'$ represent the counts taken on the samples drawn from each of the N vessels, after sedimentation.

The steps in the calculation performed by the data processing unit are as follows:

(i) Convert all counts from BCD to binary numbers.
(ii) Calculate $R_n = (W_1 + W_2)/2C_n$ and $R_n' = (W_1' + W_2')/2C_n'$
for n = 1 to N.

This standardises all sample counts in terms of the mean water count.

(iii) Calculate $S_n = (R_n - 1) - \alpha(R_n - 1)^2$
and
$S_n' = (R_n' - 1) - \alpha(R_n' - 1)^2$
for n = 1 to N, where $\alpha$ is a constant.

$S_n$ and $S_n'$ are quantities which are proportional to the percentages by weight of solids in the suspensions. It is not necessary to calculate the actual percentages since ratios of these percentages only are required.

(iv) Calculate $P_n = 100(S_n'/S_n)$ for n = 1 to N.

$P_n$ is the percentage by weight of particles in suspension n having equivalent spherical diameters less than a given size.

(v) Convert $P_n$ from binary to BCD to nearest integer.

The accuracy obtained is about ±1%.

The result is then printed out for each sample. The print out gives the sedimentation time in minutes, followed by the reference number (up to 4 digits) of the suspension and the percentage by weight of particles in the suspension having equivalent spherical diameters less than the size corresponding to the sedimentation time. If further size determinations are performed on the same suspensions, there then follows the second sedimentation time, the reference numbers and percentages and the third sedimentation time, reference numbers and percentages.

The data processing unit most conveniently comprises a microcomputer having a microprocessor as its central processing unit, which also controls automatically the sequence and timing of each step in the procedure. The control system may include a unit which gives a visual and/or audible warning if, for any reason, the sequence of operations is suspended other than during the sedimentation period, and means for giving a warning if incorrect data is keyed into the processing unit, for example if a number having 2 or more digits is keyed in for the number of size determinations or a number having 4 or more digits is keyed in for the sedimentation time.

Figure 3:
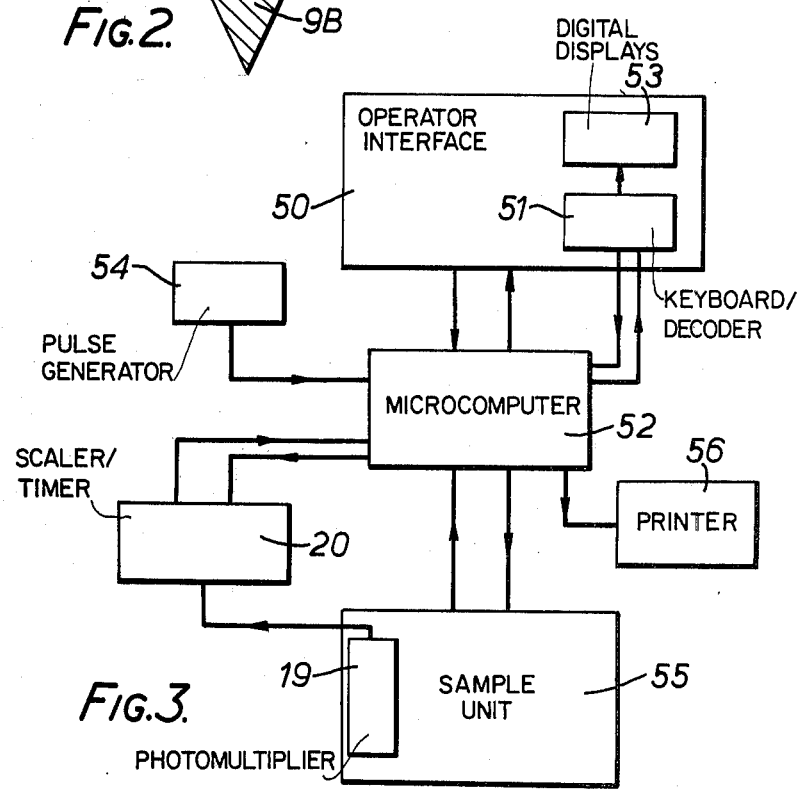
FIG. 3 is a block diagram of a control system for the embodiment.

A block diagram of a suitable control system for the apparatus is shown in FIG. 3.

The operator interface 50 comprises a keyboard/decoder 51 for entering into the memory of a microcomputer 52 the number of size determinations required, the appropriate sedimentation times and the suspension reference numbers. Digital displays 53 are provided for confirming the numbers entered by the keyboard/decoder 51 and the total number of samples. The operator interface 50 also comprises on/off switches for the power supplies and for the pump 14, an auto/manual switch and push buttons (not shown) for operating the apparatus manually. An alarm (not shown) is also included in this interface 50 together with a number of light emitting diodes (LED's) which indicate the status or stage reached by the program. A pulse generator 54 provides timing pulses for advancing the water bath 2 by means of the stepping motor 6 and for determining the sedimentation time.

One set of LED's indicate whether (a) the pulse generator 54 is working, (b) the test container 15 is full, (c) the sampling tube 9 is lowered, (d) the apparatus is in the "start" position, (e) the apparatus is "ready to start", (f) the apparatus requires the sedimentation time to be entered by means of the keyboard/decoder 51, (g) the program is halted for any reason, and (h) the end of a complete run on a given batch of suspensions has been reached. A second set of LED's indicates whether (a) the sampling tube 9 is being raised, (b) the sampling tube 9 is being lowered, (c) the vacuum valve 25 is open, (d) the positive air pressure valve 30 is open, (e) the water valve 25 is open, (d) the positive air pressure valve 30 is open, (e) the water valve 28 is open, (f) the drain valve 34 is open, (g) the mixing means is operating, and (h) the water bath 2 is being advanced by the stepping motor 6.

A further set of push buttons is labelled "Start", "Halt", "Reset" (to clear the number of size determinations, the sedimentation times and the reference numbers from the memory locations), "Alarm Cancel", "Repeat Print" (for providing duplicate copies of the print-out of results) and "Debug" (for bringing into action a special fault-finding program when necessary).

The scaler/timer 20 determines the time interval over which pulses from the photomultiplier 19 are counted and divides the count by ten or other suitable factor. While the count is in progress the scaler/timer 20 sends a "busy" signal to the microcomputer 52 to indicate that it is not yet ready for the next count. A multiposition switch (not shown) is provided to select manually the time interval over which pulses are counted and a digital display of the count is provided.

A sample unit 55 contains three motors and four valves which are actuated by signals from the microcomputer 52. The motors are the stepping motor 6 for advancing the water bath 2, a motor for raising and lowering the sampling tube 9 by means of the rack 11 and pinion 12, and a motor for driving the mixing means. The valves are the vacuum valve 25, the water valve 28, the positive air pressure valve 30 and the drain valve 34, all of which are operated by solenoids. The air bleed valves 31 and 32 are preset to provide a suitable small opening which remains unchanged unless the performance of the pump 14 alters. Signals are fed from the sample unit 55 to the microcomputer 52 from level probe 13 which indicates when the sampling tube 9 is at the correct depth, level probe 35 which indicates when the test container 15 is full and reed switch 41 which is actuated by the magnet 42 to stop rotation of the water bath 2 when the first vessel 1 is again under the sampling tube. A printer 56 is provided for printing out the results.

The apparatus described above with reference to the drawings is advantageous since it enables the completely automatic determination of particle size data for a plurality of samples at the same time.

I claim:

1. Apparatus for determining the proportion of particles having a size of less than a predetermined size in a fluid suspension, which apparatus comprises:
   (a) at least one vessel for containing a fluid suspension;
   (b) mixing mean for thoroughly mixing the suspension in said vessel;
   (c) a container connected to sampling means;
   (d) transfer means for enabling said sampling means to selectively withdraw samples of the suspension from a predetermined level within said vessel and for transferring the samples to the container before and after settling for a preselected time in the vessel respectively, the relationship between said predetermined level and preselected time being such as to permit particles of said predetermined size to sink from the surface of the suspension to said predetermined level according to Stokes' law;
   (e) monitoring means for monitoring the particle concentration within the container to produce an output dependent on said concentration; and
   (f) control means for controlling the transfer means (i) so that the sampling means withdraws from said vessel a first sample of thoroughly mixed suspension from said predetermined level and the first sample is transferred to the container for monitoring and for draining and flushing the first sample after monitoring, and (ii) so that the sampling means withdraws from said vessel a second sample of suspension taken from the same predetermined level as was the first sample for monitoring after allowing the suspension in said vessel to settle for said preselected time sufficient to enable particles of said predetermined size to sink from the surface of the suspension to said predetermined level within the vessel according to Stokes' law and the second sample is transferred to the container for monitoring; said control means being adapted to determine the proportion of particles having a size of less than said predetermined size in the fluid suspension using the outputs from said monitoring means resulting from monitoring of the first and second samples.

2. Apparatus according to claim 1, wherein a plurality of said vessels for containing fluid suspensions are provided and the control means is adapted to control the transfer means (i) so that the sampling means withdraws a first sample of suspension from each vessel in turn and each first sample is transferred to the container for monitoring and (ii) so that the sampling means withdraws a second sample of suspension from each vessel in turn after said time and each second sample is transferred to the container for monitoring.

3. Apparatus according to claim 2, wherein the sampling means includes a sampling tube and motor means for placing each vessel in turn below the sampling tube.

4. Apparatus according to claim 3, wherein the vessels are arranged about a circle and the motor means is adapted to rotate the arrangement of vessels to bring each vessel in turn below the sampling tube.

5. Apparatus according to claim 4, wherein the motor means comprises a stepping motor.

6. Apparatus according to claim 3, wherein the sampling means further includes lowering means for lowering the inlet of the sampling tube to said predetermined level within each vessel.

7. Apparatus according to claim 6, wherein the lowering means comprises a rack and pinion.

8. Apparatus according to claim 6, the fluid suspension being electrically conductive, wherein the lowering means includes a probe which is adapted to contact the surface of the fluid suspension in a vessel when the inlet of the sampling tube reaches said predetermined level.

9. Apparatus according to claim 3, wherein the sampling tube is closed at its lower end and the inlet is in the form of a plurality of holes in the curved wall of the tube in the vicinity of its lower end, the holes being distributed about the circumference of the tube such that all the holes lie at said predetermined level during sampling.

10. Apparatus according to claim 2, wherein the mixing means comprises a motor-driven magnet external to said vessels and a magnet follower within each of said vessels.

11. Apparatus according to claim 1, wherein the monitoring means comprises an x-ray source for passing x-rays through a sample in the container and an x-ray detector for detecting the x-rays which emerge from the container, under control of the control means, at least parts of the container being transparent to x-rays.

12. Apparatus according to claim 1, wherein the mixing means comprises a motor driven magnet external to said vessel and a magnet follower within said vessel.

13. Apparatus according to claim 1, wherein the transfer means includes a pump coupled to the container for providing suction to draw samples into the container.

14. Apparatus according to claim 13, wherein the pump is also adapted to apply positive pressure to the interior of the container so as to discharge samples from the container by way of a valve.

15. Apparatus according to claim 1, wherein means are provided for supplying water to the container.

16. Apparatus according to claim 1, wherein said vessel is contained in a temperature-controlled bath.

17. Apparatus according to claim 1, wherein the control means is adapted to calculate the percentage by weight of particles of less than said predetermined size in said fluid suspension from the readings obtained by monitoring two samples of that suspension in the container.

18. Apparatus according to claim 1, wherein the control means comprises a digital data processing unit.

* * * * *